United States Patent
Thomann et al.

(10) Patent No.: US 6,933,719 B2
(45) Date of Patent: Aug. 23, 2005

(54) FLUID FLOW PROPERTIES FROM ACOUSTICALLY STIMULATED NMR

(75) Inventors: Hans Thomann, Bedminster, NJ (US); Minyao Zhou, Somerville, NJ (US)

(73) Assignee: ExxonMobil Research and Engineering Co., Annandale, NJ (US)

( * ) Notice: Subject to any disclaimer, the term of this patent is extended or adjusted under 35 U.S.C. 154(b) by 0 days.

(21) Appl. No.: 10/871,115

(22) Filed: Jun. 18, 2004

(65) Prior Publication Data

US 2005/0007109 A1 Jan. 13, 2005

Related U.S. Application Data

(60) Provisional application No. 60/485,000, filed on Jul. 3, 2003.

(51) Int. Cl.$^7$ ................................. G01V 3/00
(52) U.S. Cl. ...................... 324/303; 324/306
(58) Field of Search ................. 324/303, 306, 324/300, 307, 309

(56) References Cited

U.S. PATENT DOCUMENTS

| | | | |
|---|---|---|---|
| 5,428,291 A | * | 6/1995 | Thomann et al. ........... 324/303 |
| 6,518,758 B1 | | 2/2003 | Speier et al. ............... 324/303 |
| 6,528,995 B1 | | 3/2003 | Speier et al. ............... 324/303 |
| 6,531,869 B1 | | 3/2003 | Speier et al. ............... 324/303 |
| 6,538,438 B1 | | 3/2003 | Speier et al. ............... 324/303 |
| 6,642,715 B2 | | 11/2003 | Speier et al. ............... 324/303 |
| 6,710,596 B2 | | 3/2004 | Pop et al. ................... 324/303 |
| 2003/0052672 A1 | | 3/2003 | Speier et al ................ 324/303 |
| 2003/0052673 A1 | | 3/2003 | Speier et al. ............... 324/303 |
| 2003/0052674 A1 | | 3/2003 | Speier et al. ............... 324/303 |
| 2003/0052675 A1 | | 3/2003 | Speier et al. ............... 324/303 |
| 2003/0214287 A1 | | 11/2003 | Sun et al. ................... 324/303 |

* cited by examiner

Primary Examiner—Louis Arana
(74) Attorney, Agent, or Firm—Ronald D. Hantman

(57) ABSTRACT

This invention is a method to measure fluid flow properties of a porous medium, including, but not limited to, the fluid flow permeability. In a preferred embodiment, the measurements are made down hole in drill wells exploring for hydrocarbons or acquifers. The measurement involves two types of instruments. One instrument creates a pressure wave in the porous medium, which generates motion of the fluid in the pore space. The second instrument measures the fluid motion in the pore space using Nuclear Magnetic Resonance (NMR) methods. Any type of instrument that can generate a pressure gradient is suitable, including instruments that are remote from the NMR instrument.

Magnetic field gradients can be used to localize the NMR signal to a specific region within the porous medium. The magnetic field gradient also provides the method by which the fluid motion is encoded on to the NMR signal. The permeability is calculated from the known pressure gradient present in the porous medium by virtue of the applied pressure gradient or pressure wave and the velocity of the fluid in the rock pore space as measured by NMR.

19 Claims, 4 Drawing Sheets

Acoustically Stimulated NMR Logging Measurement

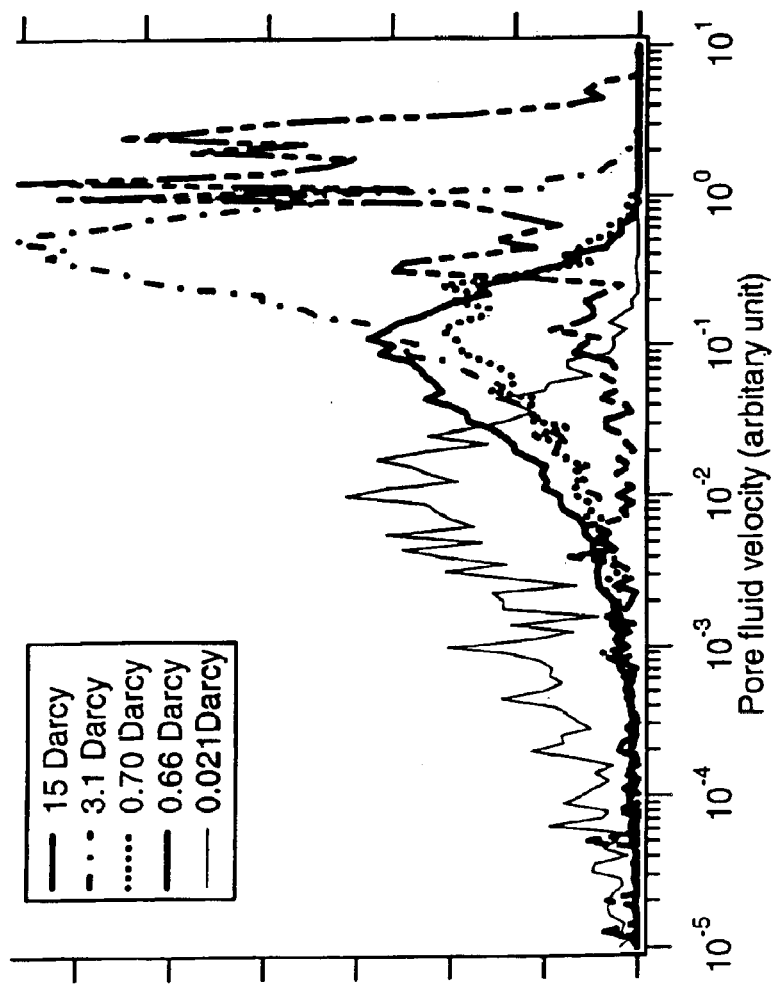
Figure 2: Calculated velocity distribution functions for reservoir rocks with different permeabilities. The calculation is performed using the real three dimensional pore space structure determined by x-ray micro-tomography as described in the Detailed Description of the Invention

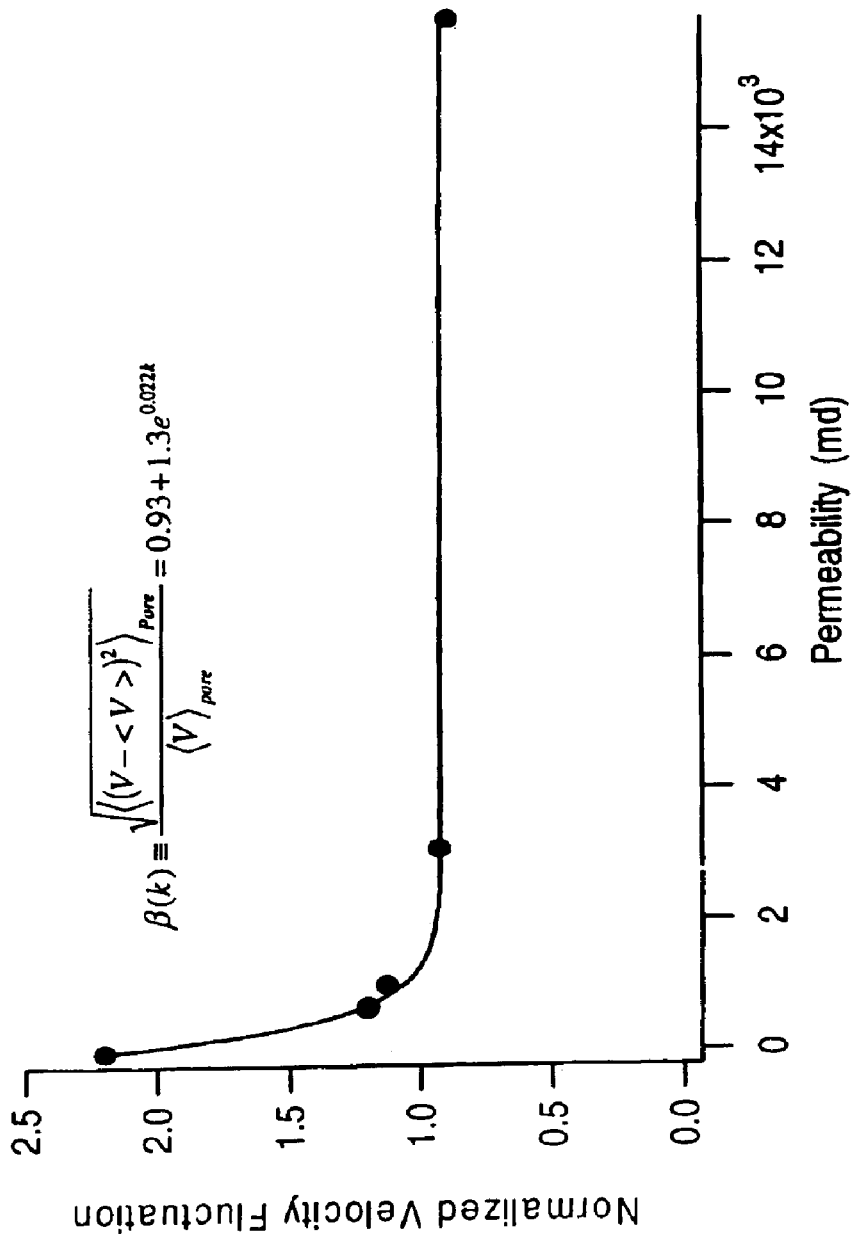
Figure 3: Normalized velocity variation as a function of permeability. The normalized velocity variation is a ratio of pore velocity variation to he mean pore flow velocity

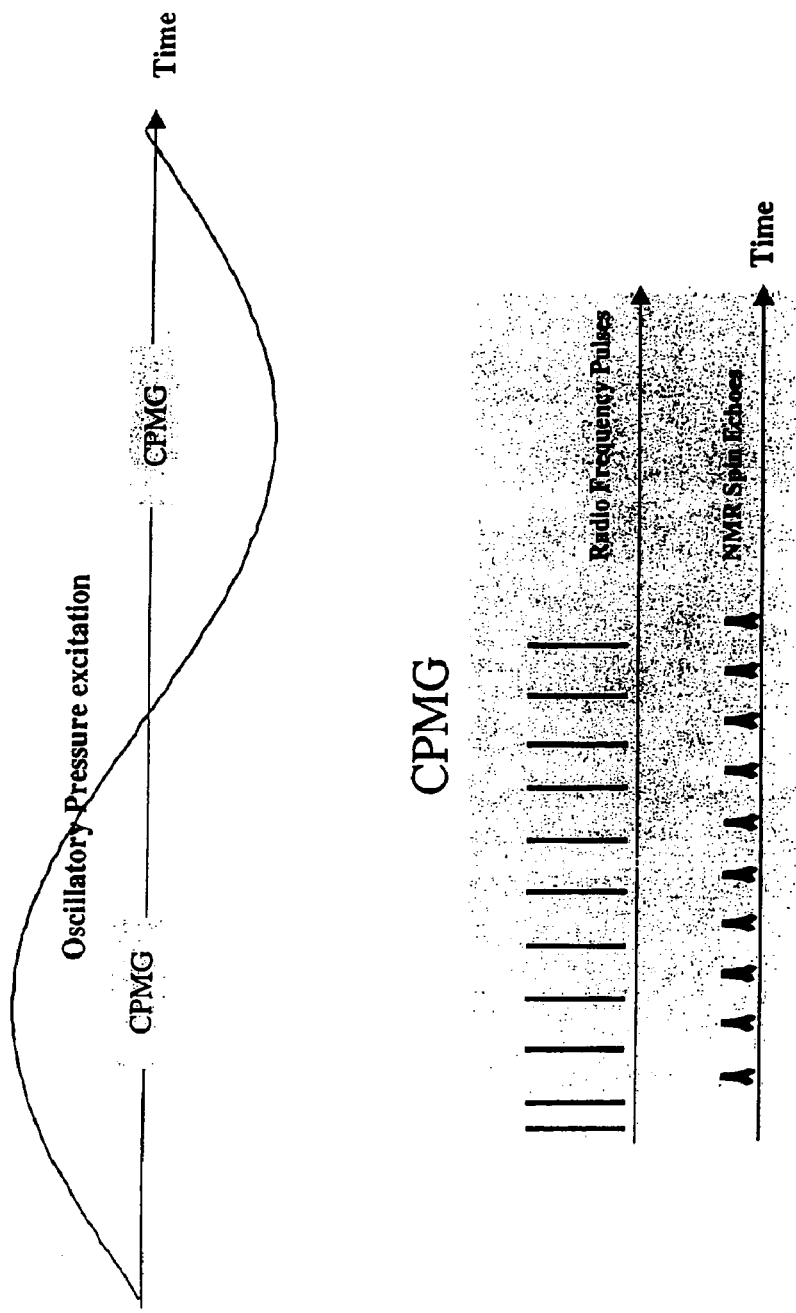
Fig. 4: Timing sequence for measurements at low acoustic frequencies using a sinusoidal acoustic wave

FLUID FLOW PROPERTIES FROM ACOUSTICALLY STIMULATED NMR

This application claims the benefit of U.S. Provisional application 60/485,000 filed Jul. 3, 2003.

BACKGROUND OF THE INVENTION

One of the major objectives of open hole logging in hydrocarbon exploration wells is to evaluate the fluid flow properties of the reservoir. Flow properties of particular interest include the relative fluid saturation at a given capillary pressure, the fluid flow permeability, the fluid viscosities, and the volume of bound formation water. The capillary bound water saturation determines the volume fraction of water in the pore space that will flow from the rock. This volume fraction subtracted from the total rock pore volume provides a measure of the maximum producible oil volume. The fluid flow permeability indicates how fast the fluid will flow through the rock for a given pressure gradient. These fluid flow properties are required to determine the economics of the reserve and for field development planning, such as the number of wells, well spacing, surface facilities, pipeline facilities, etc, which will be needed for production.

At present three methods are used for determining the reservoir rock fluid flow parameters: (1) formation micro-test and well testing; (2) coring and core analysis, and (3) inference from well logging measurements. Formation micro-testing and well testing involve the actual production of reservoir fluids from a specific reservoir interval. The disadvantage of this method is its high cost and that the flow parameters are only obtained over small reservoir intervals. The second option is to cut cores and determine the flow properties by laboratory core analysis measurements. This procedure is costly and reservoir flow parameters are only determined for selected reservoir intervals where cores from which cores are cut. There is also an additional uncertainty introduced on the measured flow parameters because of the possibility that the fluids redistribute in the pore space when the core is removed from the reservoir. The third option is to infer fluid flow parameters from logging measurements. This has the advantage of providing continuous data over the large reservoir intervals at much lower cost. The major disadvantage is that the fluid flow properties of the reservoir are inferred from measurements on non-flowing fluids, rather than measured directly on fluid flowing in the rock.

The fluid flow permeability, $\kappa$, is defined by Darcy's law:

$$\upsilon = -(\kappa/\eta)\nabla P \qquad (1)$$

where $\upsilon$ is the flow velocity, $\nabla P$ is the pressure gradient and $\kappa/\eta$, the ratio of permeability to viscosity, is the fluid mobility. At present the only direct measurement of permeability is obtained by laboratory core analysis. In these laboratory measurements the viscosity of the fluid and pressure gradient are known and the velocity is measured. The permeability is then readily derived from data fitting using the Darcy law definition of permeability. By contrast, permeabilities derived from well testing and repeat formation testers are not measured directly but rather are derived from modeling the data from these measurements. In general, the experimental control parameters such as fluid velocity, viscosity, and pressure gradient are not known and must be included in the fit parameters of the model. The model must also include other parameters such as the pressure gradients in the reservoir and the radial flow profiles that control bulk flow into the borehole. This large number of fit parameters has the consequence of introducing large uncertainties in the estimation of the permeability.

Wire line logging tools have the advantage that data can be quickly and comparatively inexpensively obtained over very large reservoir intervals. This is especially important early in the appraisal stage of exploration wells where logging data is used to identify reservoir intervals where the more expensive well tests or formation micro-tests measurements will be made. The major disadvantage of all continuous log wire line tools is that the fluid permeability is not directly measured but is inferred from other petrophysical properties of the reservoir rock. Permeabilities are derived using empirical correlations established from laboratory measurements of permeability on cores and the characteristic tool response parameters. The primary tools used for this type of analysis are the sonic, electrical conductivity, and nuclear magnetic resonance (NMR) logging tools. For the sonic measurements, the permeability is derived from the attenuation of the elastic wave propagating along the borehole or in the formation. A major complication is that the attenuation is determined by the bulk properties, which includes both the grain and fluid properties. For the conductivity measurements, the permeability is derived using the Kozeny-Carmen relationship. A major complication in this measurement is that the conductivity varies with salinity as well as the relative saturation of hydrocarbons and also depends on the amount and types of clays and minerals present. For the NMR measurements, the permeability is inferred from an assumed simple relation between the NMR relaxation time distribution and the pore size distribution. However this relationship is complex and the NMR relaxation time spectrum can only be converted to a pore size distribution in ideal circumstances when all relevant parameters such as the surface relaxivity and contributions of the pore-to-pore coupling are known. As a result of the complications in the interpretation of each of these measurements, the permeability inferred from the data analysis is bounded by large uncertainties.

The present invention describes a method to determine fluid flow velocities in the reservoir rock in the presence of a known pressure gradient. The analysis of the data to determine permeability does not require assumptions about bulk flow into the borehole such as required for the analysis of well test and formation micro-test data. The measurement is also made using a wire line tool under continuous logging conditions so that data over large reservoir intervals are obtained.

SUMMARY OF THE INVENTION

This invention is a method to measure reservoir rock fluid flow properties, including but not limited to the fluid flow permeability. In a preferred embodiment, the measurements are made down hole in drill wells exploring for hydrocarbons or acquifers. Two types of instruments are lowered into the drill well as shown in FIG. 1. One instrument creates a pressure gradient in the reservoir rock. This pressure gradient can be created by pressure waves, which can be pulsed or oscillatory with a variable frequency including zero, i.e., a steady state pressure gradient. In each case the pressure gradient creates a fluid flow in the reservoir rock. The temporal and spatial characteristics of the fluid flow velocity depend on the details of the method used to create the pressure gradient, however, in all cases the fluid motion in the reservoir rock is detected by NMR measurements. Magnetic field gradients can be used to localize the origin of the NMR signal to a specific region within the rock. The magnetic field gradient also provides the method by which the fluid motion is encoded on the NMR signal. The permeability is then calculated from the known pressure gradient present in the rock by virtue of the applied pressure gradient or pressure wave and the velocity of the fluid in the rock pore space measured using NMR.

BRIEF DESCRIPTION OF THE FIGURES

FIG. 2 shows a calculated velocity distribution functions for reservoir rocks with different permeabilities. The calculation is performed using the real three dimensional pore space structure determined by x-ray micro-tomography as described in the Detailed Description of the Invention FIG. 3 shows a normalized velocity fluctuation as a function of permeability. The normalized velocity variation is a ratio of pore velocity variation to the mean pore flow velocity.

FIG. 4 shows a one possible timing sequence for the pressure wave, radio frequency pulses, and NMR spin echo signals when low frequency pressure waves are used.

DETAILED DESCRIPTION OF THE INVENTION

Figure 1:
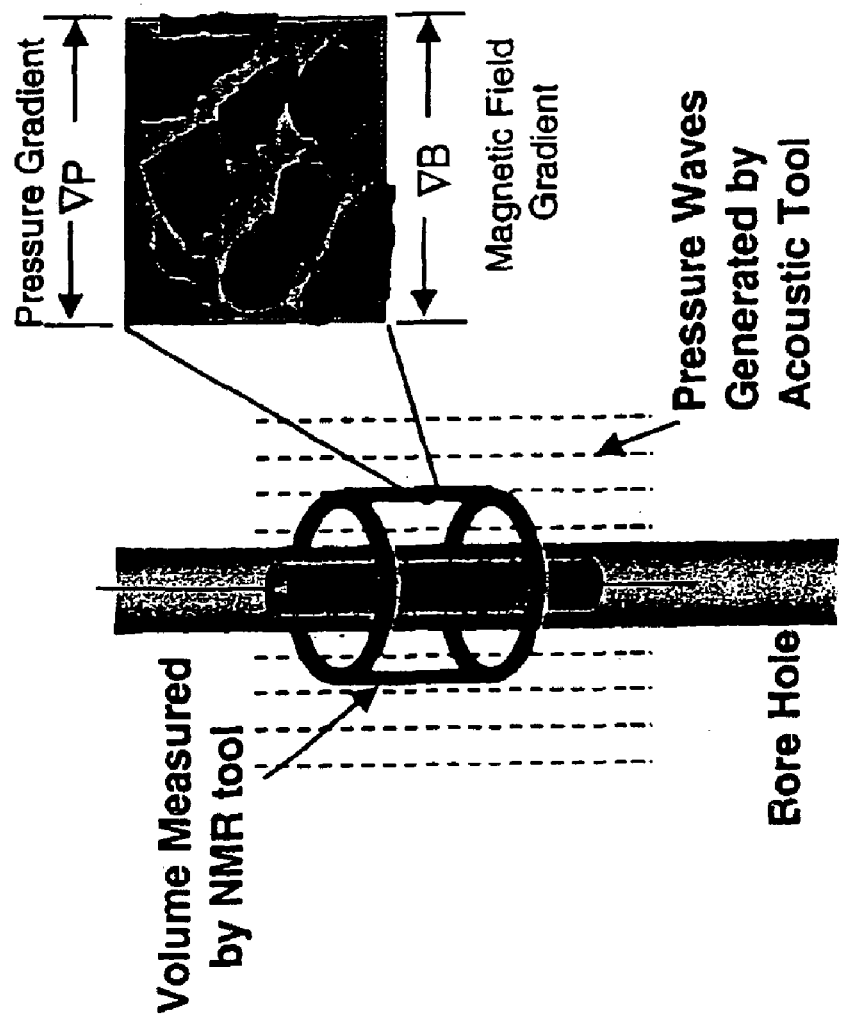
FIG. 1 shows a schematic of the acoustically stimulated NMR measurement.

The invention disclosed here describes methods that determine formation permeability by measuring NMR signals that respond to pressure gradients created by acoustic stimulation in the bore hole. These pressure gradients create motion of fluids in the rock pore space of the rocks in the formation surrounding the bore hole. In the case of hydraulic contact between the fluid in the borehole and the fluid in the formation rock, the displacement of the fluid in the borehole creates the displacement of the fluid in the formation rock. This is frequently referred to as the squirt boundary condition.

Motion of the fluid in the formation rock can also be created when there is no direct hydraulic contact between the fluid in the borehole and the fluid in the formation rock. Hydraulic contact between these fluids can be broken by the presence of an impermeable barrier at the bore hole wall. This can for example be created by the deposition of drilling mud on to the bore hole wall or damage to the rock structure near the bore hole wall as a result of the drilling process. The presence of an impermeable barrier between the two fluids creates what is sometimes known as a no-squirt boundary condition. In this case, fluid motion of the fluid in the formation rock can be created by a propagating compressional wave generated in the bore hole. The permeability is then determined from the displacement of the fluid in the formation rock relative to the rock matrix. This fluid displacement is determined using NMR measurements as described by the procedures of the present invention.

The description of the invention includes three components: theory, procedures of down-hole implementation, and procedures of data processing.

Theory

Current NMR tool measure NMR signals such as spin echoes which are used to determine NMR relaxation times that carry the information on the rock and fluid properties. The NMR relaxation rates are primarily controlled by the thermal motion of the fluid molecules and the collision of the fluid molecules with the internal surface of the pores in the rock. It is well known that the relaxation rate of Carr-Purcell-Meiborn-Gill (CPMG) echo train includes three terms[1,2,3]

$$1/T_2 = 1/T_{2B} + 1/T_{2S} + \frac{1}{3}\gamma^2 G^2 \tau^2 D_{\text{eff}} \qquad (2)$$

where first term is the contribution from the fluid bulk relaxation mechanism, the second term represents the surface relaxation at the fluid-matrix interface and the last terms reflects the relaxation due to diffusion in the presence of a magnetic field gradient, $G$, where time $\tau$ refers to the time delay between the radio frequency pulse and the refocusing RF pulse in the spin echo pulse sequence and $\gamma$ is the nuclear gyromagnetic ratio. When fluid moves relative to the formation matrix, our theoretical analysis shows that there is an additional relaxation due to the coupling between fluid flow and the applied field gradient G, which we denote as the acoustic NMR relaxation rate $1/T_{2a}$. The theoretical analysis (see Appendix for details) is comprised of the following three steps.

First, the NMR calculation shows that the phase change of the transverse magnetization (which is proportional to the NMR signal) in response to an oscillatory flow motion during one echo time is proportional to the mean velocity of the absolute motion, $$\langle \Phi(2\tau) \rangle = \frac{\gamma G}{\omega^2} F(\omega\tau, \phi_0) \langle V(\omega) \rangle \qquad (3)$$

while the normalized amplitude of the transverse magnetization is proportional to the fluctuation of the pore flow velocity, $$\left| \frac{M(2\tau)}{M(0)} \right| = 1 - \frac{[\gamma G F(\omega\tau, \phi_0)]^2}{2\omega^4} \langle (\Delta V)^2 \rangle_{pore}. \qquad (4)$$

In Eq3 and 4, the function F is defined as $$F(\omega\tau,\phi_0) = \cos\phi_0 - 2\cos(\omega\tau+\phi_0) + \cos(2\omega\tau+\phi_0), \qquad (5)$$

where $\phi_0$ is the initial phase of acoustic oscillation at the start of a CPMG sequence. Both the phase change and the amplitude change decrease rapidly with increasing frequency. In the low frequency limit, such that $\omega\tau \ll 1$, Eq. 5 reduces to the more simple expression, $$F(\omega\tau,\phi_0) \approx \omega^2 \tau^2 \cos\phi_0. \qquad (6)$$

Using Eq. 4, we obtain an analytical form for the acoustic NMR relaxation rate, $$\frac{1}{T_{2a}} = \frac{1}{4}\gamma^2 G^2 \tau^3 \cos^2\phi_0 \langle (\Delta V)^2 \rangle_{pore}. \qquad (7)$$

In the second component of the theory, we use a pore network created from the x-ray Computed Tomography images of real rocks to calculate the fluctuation of velocities in the pores in response to an applied pressure gradient. From these simulations, we find that the velocity fluctuation is proportional to the applied pressure gradient, consistent with Darcy's Law, $$\sqrt{\langle \Delta V^2 \rangle_{pore}} = \frac{\beta(k)}{\phi}|\langle V \rangle| = \frac{\beta(k)}{\phi}\frac{k}{\eta}\left|\frac{dP}{dx}\right| \qquad (8)$$

where $\beta(k)$ is a number between 1 and 2 with a weak permeability dependence (see FIG. 2 and FIG. 3), and $\phi$ is the porosity of the rock. This expression relates the fluctuation of the velocities for the fluid in the pore space, which is measured by NMR, to the local applied pressure gradient.

The third component of the theory relates the local pressure gradient to the pressure, $P_o$, applied in the bore hole. This relation is a function of the contact boundary conditions, described above, between fluid in the borehole and the fluid in the formation. If the formation fluid is in hydraulic contact with bore hole fluid (i.e., the squirt boundary condition), the local pressure gradient for a small offset x, relative to the wall of the borehole, can be estimated from, $$\frac{dP(x,t)}{dx} \approx -\frac{P_o}{\lambda}[\sin(\omega t + x/\lambda) + \cos(\omega t + x/\lambda)]\exp\{-x/\lambda\} \quad (9)$$

where $\lambda$ is the pressure excitation penetration length which depends on the excitation frequency, $k/\eta$ is the formation fluid mobility, and M is the effective fluid modulus. Biot theory[4] defines the relationship between these parameters, $$\lambda = \sqrt{2Mk/\omega\eta}. \quad (10)$$

Using the relationships in Eq's. 7, 8 and 9, we obtain the acoustic NMR relaxation rate which applies for the squirt boundary conditions and for low frequency acoustic excitation, $$\frac{1}{T_{2a}(x)} = \frac{1}{4}\gamma^2 G^2 \tau^3 \left(\frac{\beta(k)}{\phi}\frac{k}{\eta}\frac{P_o}{\lambda}\right)^2 \cdot [1 + \sin(2x/\lambda)]\exp(-2x/\lambda). \quad (11)$$

The acoustic NMR relaxation rate under such squirt boundary conditions is a function of the offset x from the borehole wall with just two unknown parameters, the formation fluid mobility $k/\eta$ and the penetration length $\lambda$. A NMR tool with multi-sensitive-volumes, receiving spin echoes from multi offsets, would recover the penetration length in the target formation, and the amplitude of acoustic NMR relaxation rate would directly give an estimate of formation fluid mobility.

For the non-squirt boundary condition, the borehole pressure excitation generates a fast P wave in the formation, which creates an oscillatory displacement of the formation matrix together with pore fluid in the matrix. The mean velocity of the pore fluid is a sum of the matrix velocity and the mean velocity of fluid motion relative to the matrix, $$\langle V \rangle = V_m + \langle V_r \rangle, \quad (12)$$

which can be observed by calculating the phase change of NMR. In the low frequency limit, by setting $\phi_0(x) = \omega x/v_P$, we have $$\text{Phase}(M(2\tau)/M(0)) \approx \gamma G \tau^2 \cos(\omega x/v_P)\langle V \rangle \approx \gamma G \tau^2 \langle V \rangle \quad (13)$$

where $v_P$ is the P wave velocity and the last step reflects the fact that the offset is much smaller than the wave length of the fast P wave. In Eq. 12, the relative fluid velocity is orders of magnitude smaller than the matrix velocity so that the phase shift of the NMR signal is dominated by the motion of the fluid with the matrix. However, based on the Biot theory[4], the relative flow velocity is proportional to the matrix velocity and the proportionality coefficient contains the information for the formation mobility, $$\langle V_r \rangle = i\frac{k\omega \rho_f}{\eta} V_m \quad (14)$$

The acoustic NMR relaxation rate, Eq. 7, is a function of the velocity fluctuation for the fluid in the pore space. The pore network simulation establishes the simple relationship, Eq. 8, between the mean relative flow velocity and the velocity fluctuation for fluid in the pore space. Using these relationships, we can estimate the formation fluid mobility by the acoustic NMR measurement alone with additional information on fluid density, which could be obtained from other independent measurements, such as neutron or resistivity logging.

Implementation

One possible implementation would be to use an NMR tool with multi-sensitive-volumes [5] in which two echo or CPMG measurements can be made at each downhole location. One NMR measurement is made under normal conditions and one NMR measurement is made in the presence of an applied pressure gradient generated by a pressure source. This pressure source could be located at the well bore surface or it could be located down hole near the location of the NMR instrument.

The frequency of pressure excitation should be chosen to make the penetration length not too small compared to the offset of the NMR sensitive volume. In the case of NMR spin echoes, the echo spacing should be large enough so that the gradient related NMR relaxation dominates over the surface relaxation. An example of a timing sequence for the pressure wave, radio frequency pulses, and NMR spin echo signals detected is shown in FIG. 4.

Data Processing

One procedure for determining the formation fluid mobility which is applicable under the squirt boundary condition includes the follow four steps:

1. Calculate the mean CPMG relaxation rate for each measurement;
2. Obtain the acoustic NMR relaxation rate by subtracting the CPMG relaxation rate with no pressure excitation from one with pressure excitation;
3. Fit the acoustic NMR relaxation rate as a function of offset x with a fitting form $y(x) = C(1 + \sin(\alpha x))\exp(-\alpha x)$, where C and $\alpha$ are two fitting parameters. Best fitting gives right number for both C and $\alpha$, which are denoted as C' and $\alpha'$.
4. Estimate the penetration length and formation flow mobility in terms of $$C' = \frac{\tau^3}{4}\left(\gamma G \frac{\beta}{\phi}\frac{k}{\eta}\frac{P_0}{\lambda}\right)^2 \text{ and } \alpha' = \frac{2}{\lambda}$$

One procedure for determining the formation fluid mobility which is applicable under the no-squirt boundary condition includes the following alternate steps after step 2 above:

3. Determine the velocity fluctuation $\langle(\Delta V)^2\rangle$ from the acoustic NMR relaxation rate, Eq. 7.
4. Calculate the phase difference between the two measurements with and without pressure excitation. The phase difference will accumulate linearly with increasing number of echoes and the slope gives the mean velocity of matrix motion $V_m$.
5. Calculate the formation flow mobility using Eq. 8 and 14, where $V_r = V$:

$$\frac{k}{\eta} = \frac{\phi}{\beta\omega\rho_f}\frac{\sqrt{\langle(\Delta V)^2\rangle}}{V_m}$$

DETAILED DESCRIPTION OF THE PREFERRED EMBODIMENTS

NMR Response to Fluid Flow

The effect of flow is to introduce an additional relaxation mechanism. In the anticipation of considering the effect of oscillatory flow, we consider the phase change for one nuclear spin undergoing a displacement in the time interval from t=0 to t=2$\tau$:

$$\Phi(2\tau) = -\gamma G\left[\int_0^\tau x(t)dt - \int_\tau^{2\tau} x(t)dt\right] \quad (15)$$

where the displacement is given by:

$$x(t) = \int_o^t V(t')dt'. \quad (16)$$

Here, the displacement and velocity of the nuclear spin corresponds to those components along the direction of the applied magnetic field gradient. The nuclear spin velocity is a superposition of medium velocity $V_m$ plus a relative velocity $V_r$ of the fluid motion relative to the matrix:

$$V(t)=V_m(t)+V_r(t). \quad (17)$$

The corresponding phase shift of the transverse NMR magnetization can then be divided into two terms:

$$\Phi(2\tau)=\Phi_m(2\tau)+\Phi_r(2\tau) \quad (18)$$

A normalized NMR response is given by:

$$\frac{M(2\tau)}{M(0)} = \langle\exp[-i\Phi(2\tau)]\rangle = \langle\cos[\Phi(2\tau)]\rangle + i\langle\sin[\Phi(2\tau)]\rangle \quad (19)$$

where the average is taken over all spins. Assuming that the spin phase change is much less than 1, Eq. 19 can be expanded in terms of $\Phi$. Keeping terms up to second order, we have:

$$\frac{M(2\tau)}{M(0)} \cong 1 - \frac{1}{2}\langle\Phi^2(2\tau)\rangle + i\langle\Phi(2\tau)\rangle. \quad (20)$$

We are interested in the magnitude of the NMR response which is given by:

$$\left|\frac{M(2\tau)}{M(0)}\right| \cong \sqrt{\left\{1 - \frac{1}{2}\langle\Phi^2(2\tau)\rangle\right\}^2 + \langle\Phi(2\tau)\rangle^2} \quad (21)$$

$$\approx 1 - \frac{1}{2}\{\langle\Phi^2(2\tau)\rangle - \langle\Phi(2\tau)\rangle^2\}$$

$$= 1 - \frac{1}{2}\{\langle\Phi_r^2(2\tau)\rangle - \langle\Phi_r(2\tau)\rangle^2\}$$

The second step in Eq. 21 indicates that the magnitude of normalized NMR signal is determined by the spin phase fluctuation. The motion of the medium induces a uniform spin velocity and therefore results in a uniform phase change that does not contribute to the relaxation of NMR signal. Therefore, only the relative flow motion contributes in the third step of the Eq. 21.

NMR Response to Oscillatory Fluid Flow

The velocity of a spin subject to a pressure gradient at a single frequency can be described as:

$$V(t)=V(\omega)\cos(\omega t+\phi_0). \quad (22)$$

Inserting Eq. 22 into Eq. 15, we have $$\Phi(2\tau) = \frac{\gamma G}{\omega^2}F(\omega, \tau, \phi_0)V(\omega), \quad (23)$$

with $$F(\omega,\tau,\phi_0)=\cos\phi_0-2\cos(\omega\tau+\phi_0)+\cos(2\omega\tau+\phi_0). \quad (24)$$

In the low frequency limit where $\omega\tau\ll 1$, $$F(\omega,\tau,\phi_0)=\omega^2\tau^2\cos\phi_0. \quad (25)$$

Because the spin phase shift is proportional to the spin velocity, the differential NMR response to flow, $\{M(0)-M(2t)\}/M(0)$, is proportional to the fluctuation of spin velocity, $\langle\Delta V^2\rangle=\langle V^2-\langle V\rangle^2\rangle$, that is, $$1 - \left|\frac{M(2\tau)}{M(0)}\right| = \frac{[\gamma GF(\omega,\tau,\phi_0)]^2}{2\omega^4}\langle\Delta V^2\rangle_{pore}. \quad (26)$$

The contribution of the relative fluid motion to the NMR relaxation is then given by:

$$\frac{1}{T_{2a}} = \frac{1}{4\omega^4\tau}\gamma^2 G^2 F^2(\omega,\tau,\phi_o)\langle\Delta V^2\rangle_{pore}. \quad (27)$$

In the low frequency limit, the NMR relaxation due to flow is given by $$\frac{1}{T_{2a}} = \frac{1}{4}\gamma^2 G^2\tau^3(\cos\phi_o)^2\langle\Delta V^2\rangle_{pore}. \quad (28)$$

Relation of Pore Level Fluid Flow Velocity Measured by NMR to Pressure Gradient

The flow velocity appearing in Darcy's law is the mean velocity of the fluid, $v_b$, which is an average of the flow over the whole volume while the NMR signal is a response only to the velocity of the fluid in the pore. The relationship between the bulk velocity and the pore level velocity has been determined from numerical pore network simulations.

The pore network is defined from the digital images of real rocks where the images are generated using x-ray micro-tomography. Typical digital images are volumes of 300×300×300 pixels where the resolution per pixel is between 5 to 7 microns. A pressure gradient is applied across this cube to calculate the average velocity for flow within a pore. The results show that the flow velocity varies by orders of magnitude from pore to pore. Velocity distributions calculated for a number of sandstone rocks with permeabilities spanning a range of over three orders of magnitude are shown FIG. 2.

In order to calculate the permeability, the mean flow velocity fluctuation, $\langle\Delta V^2\rangle_{pore}$, determined from NMR must be related to the velocity, $\langle V\rangle_{bulk}$, averaged over the whole medium volume. The porosity, $\phi$, relates the flow velocity average in bulk to the average over the pore volume: $\langle V\rangle_{bulk}=\phi\langle V\rangle_{pore}$. The pore network simulations were used to calculate these velocities for a variety of sandstones that had a range of permeabilities spanning over three orders of magnitude.

The normalized velocity fluctuation, defined by the ratio of $[\langle\Delta V^2\rangle_{pore}]^{1/2}$ to $\langle V\rangle_{pore}$, as a function of permeability for several sandstones is shown in FIG. 3. The ratio is of order unity and is only weakly dependent on the permeability. Darcy's law can then be written in terms of the average pore velocity fluctuation as:

$$\sqrt{\langle\Delta V^2\rangle_{pore}} = \frac{\beta(k)}{\phi}\langle V\rangle = \frac{\beta(k)}{\phi}\frac{k}{\eta}|\nabla P| \quad (29)$$

where $\beta(k)$ is a function of permeability and varies between 1 and 2. This relation provides the recipe for determining the permeability from the effect of the flow motion on the NMR relaxation rate.

NMR Response to Oscillatory Pressure Excitations

In the following, we assume that the formation fluid and borehole fluid are in hydraulic contact. Under such squirt boundary conditions, the formation fluid pressure at the surface of borehole wall is the same as the borehole pressure $P_o$. The pressure for an applied compressional wave is attenuated with the increasing offset away from the borehole wall due to geometrical spreading and to intrinsic attenuation mechanisms in the formation. For small offset, the geometrical spreading factor can be ignored so that the amplitude of fluid pressure in the formation is given:

$$P(x,t) \approx P_o \cos(\omega t + x/\lambda) \cdot \exp\{-x/\lambda\} \quad (30)$$

where $k/\eta$ is the fluid mobility (i.e., the ratio of the permeability to the viscosity), M is the effective fluid modulus, and $\lambda$ is the pressure penetration length, which is defined using Biot theory[4] by:

$$1/\lambda = \sqrt{\frac{\omega \eta}{2Mk}}. \quad (31)$$

The local pressure gradient can be calculated from the derivative of Eq. 30:

$$\frac{dP(x)}{dx} \approx -\frac{P_o}{\lambda}[\sin(\omega t + x/\lambda) + \cos(\omega t + x/\lambda)]\exp\{-x/\lambda\}, \quad (32)$$

which induces two oscillatory modes: one with initial phase $\phi_0^{(1)} = x/\lambda - \pi/2$ and another with initial phase $\phi_0^{(2)} = x/\lambda$. The acoustic NMR relaxation rate under the squirt boundary conditions can then be calculated using Eq. 28, Eq. 29 and Eq. 32:

$$\frac{1}{T_{2a}(x)} = \frac{1}{4}\gamma^2 G^2 [1 + \sin(2x/\lambda)]\tau^3 \left(\frac{\beta(k)}{\phi} \frac{k}{\eta} \frac{P_o}{\lambda}\right)^2 \exp(-2x/\lambda). \quad (33)$$

References

[1] G. R. Coates, H. J. Vinegar, P. N. Tutunjian, and J. S. Garder, 1993, "Restrictive Diffusion from Uiniform Gradient NMR Well Logging", 68th Annual Technical Conference, 3–6 October, SPE 26472
[2] M. D. Hurlimann, K. G. Helmer, T. M. De Swiet, P. N. Sen and C. H. Sotak, "Spin Echoes in a Constant Gradient and in the Presence of Simple Restriction", *Journal of Magnetic Resonance*, A113, 260–264 (1995)
[3] J. J. Howard and W. E. Kenyon, 1992, "Determination of Pore Size Distribution in Sedimentary Rocks by Proton Nuclear Magnetic Resonance", *Marine and Petroleum Geology*, Vol. 9, pp. 139–45
[4] S. R. Pride, A. F. Gangi, and F. D. Morgan, J. Acoustic. Soc. Am. 92, 3278 (1992)
[5] M. G. Prammer, J. Bouton, R. N. Chandler, E. D. Drack and M. N. Miller, "A New Multiband Generation of NMR Logging Tools", paper of SPE 49011 presented at the 1998 SPE Annual Technical Conference and Exhibition held in New Orleans, La.

What is claimed is:

1. A method to determine fluid flow properties for fluids in porous media comprising:
   (a) applying a pressure gradient by acoustic stimulation to create motion of the fluids in the porous media;
   (b) measuring the NMR signals with and without acoustic stimulation, at one or more offset positions within the porous medium away from an external surface;
   (c) determining the difference between the NMR signals by determining a phase shift and an acoustic NMR relaxation rate;
   (d) determining a fluid flow property of the porous medium from said difference of step (c).
2. The method of claim 1 wherein said motion of the fluids is oscillatory flow.
3. The method of claim 2 wherein said oscillatory flow is high frequency.
4. The method of claim 2 wherein said oscillatory flow is low frequency.
5. The method of claim 1 where the NMR signal measured is a spin echo.
6. The method of claim 1 where the NMR signal measured is a CPMG signal.
7. The method of claim 1 where the source of the pressure gradient is located at the earth's surface.
8. The method of claim 1 where the source of the applied pressure gradient is located down hole in a well bore.
9. The method of claim 1 where said fluid flow property is the fluid mobility.
10. The method of claim 1 where said fluid flow property is the permeability.
11. The method of claim 1 where said fluid flow property is the fluid viscosity.
12. The method of claim 1 where the said fluid flow property is the relative permeability.
13. The method of claim 1 wherein said method is performed under squirt boundary conditions.
14. The method of claim 13 wherein step (c) is performed by fitting the acoustic NMR relaxation rate as a function of x with a fitting form $y(x)=C(1+\sin(\alpha x))\exp(-\alpha x)$ where C and $\alpha$ are two fitting parameters, where x is the offset relative to the wall of the bore hole.
15. The method of claim 14 wherein the penetration length, $\lambda$, and formation fluid mobility, $k/\eta$ is determined.
16. The method of claim 14 wherein said penetration length and said formation fluid mobility is determined from $$C' = \frac{\tau^3}{4}\left(\gamma G \frac{\beta}{\phi} \frac{k}{\eta} \frac{P_0}{\lambda}\right)^2 \text{ and } \alpha' = \frac{2}{\lambda},$$

where $\gamma$ is the nuclear gyromagnetic ratio,

G is magnetic field gradient, $\phi$ porosity of the rock, $P_O$ is pressure amplitude, $\tau$ is time delay, $\beta$ is a number between 1 and 2.

17. The method of claim 1 wherein said method is performed under non-squirt boundary conditions.
18. The method of claim 17 wherein step (c) of claim 1 is carried out by determining the velocity fluctuation, $\Delta V$, from the acoustic relaxation rate, the mean velocity of the matrix motion, $V_m$, from the phase shift and, thereby, determining, $k/\eta$.
19. The method of claim 18 wherein $$\frac{k}{\eta} = \frac{\phi}{\beta \omega \rho_f} \frac{\sqrt{\langle (\Delta V)^2 \rangle}}{V_m},$$

Where $V_m$ is matrix velocity, $\rho_f$ is flow density, $\omega$ is angular frequency, $\phi$ is porosity of the rock, $\beta$ is a number between 1 and 2.

* * * * *